(12) United States Patent
Sawa

(10) Patent No.: US 7,320,985 B2
(45) Date of Patent: Jan. 22, 2008

(54) METHOD FOR STABILIZING ARYLCARBOXYLIC ACID, STABILIZER THEREOF AND AQUEOUS SOLUTION CONTAINING STABILIZED ARYLCARBOXYLIC ACID

(75) Inventor: Shirou Sawa, Kobe (JP)

(73) Assignee: Senju Pharmaceutical Co., Ltd., Osaka (JP)

( * ) Notice: Subject to any disclaimer, the term of this patent is extended or adjusted under 35 U.S.C. 154(b) by 736 days.

(21) Appl. No.: 10/624,674

(22) Filed: Jul. 23, 2003

(65) Prior Publication Data

US 2005/0075350 A1  Apr. 7, 2005

Related U.S. Application Data

(60) Continuation of application No. 09/885,096, filed on Jun. 21, 2001, now abandoned, which is a division of application No. 09/017,626, filed on Feb. 2, 1998, now Pat. No. 6,274,592.

(30) Foreign Application Priority Data

Feb. 4, 1997 (JP) .................................. 9-21805

(51) Int. Cl.
*A61K 31/436* (2006.01)
*A61K 31/495* (2006.01)
*A61K 31/52* (2006.01)
*A61K 47/22* (2006.01)

(52) U.S. Cl. ............... 514/291; 514/230.5; 514/253.04; 514/253.08; 514/264; 514/300; 514/312; 514/352; 514/365; 514/420; 514/567; 514/226.2; 546/89; 546/311; 546/204; 546/500; 546/501; 544/38

(58) Field of Classification Search ................ 514/291, 514/230.5, 253, 253.08, 264, 300, 312, 352, 514/365, 420, 567, 226.2; 546/89, 311, 204, 546/500, 501; 544/38

See application file for complete search history.

(56) References Cited

U.S. PATENT DOCUMENTS

| | | | |
|---|---|---|---|
| 4,794,117 A | 12/1988 | Corbiere | ..................... 514/420 |
| 5,942,508 A | 8/1999 | Sawa | |

FOREIGN PATENT DOCUMENTS

| | | |
|---|---|---|
| CA | 1 336 687 | 8/1995 |
| EP | 0 105 635 | 4/1984 |
| EP | 0 359 195 | 3/1990 |
| EP | 0 621 036 | 10/1994 |
| EP | 0 631 782 | 1/1995 |
| EP | 0 824 916 | 2/1998 |
| EP | 0 269 278 | 6/1998 |
| ES | 2 065 846 | 2/1995 |
| GB | 873 526 | 7/1961 |
| GB | 2 082 456 | 3/1982 |
| WO | 93 17716 | 9/1993 |
| WO | 95 07082 | 3/1995 |
| WO | 96 29997 | 10/1996 |
| WO | 96 32941 | 10/1996 |
| WO | 97 49405 | 12/1997 |

OTHER PUBLICATIONS

Patent Abstracts of Japan, vol. 1997, No. 04, Apr. 30, 1997 & JP 08 333246.
Patent Abstracts of Japan, vol. 1997, No. 04, Apr. 30, 1997 & JP 08 333265.
Chemical Abstracts, vol. 122, No. 26, Jun. 26, 1995, Abstract No. 322527.
Patent Abstracts of Japan, vol. 1997, No. 10, Oct. 31, 1997 & JP 09 157162.
Patent Abstracts of Japan, vol. 1995, No. 07, Aug. 31, 1995 & JP 07 097325.
Kohno et al., Chemical Abstracts, vol. 121, abstract 221074 (1994).
Nozaki et al., Chemical Abstracts, vol. 115, abstract 24529 (1991).
Duerckheimer et al., Chemical Abstracts, vol. 109:110274, 1988.

*Primary Examiner*—James O. Wilson
*Assistant Examiner*—Paul V. Ward
(74) *Attorney, Agent, or Firm*—Wenderoth, Lind & Ponack, L.L.P.

(57) ABSTRACT

A method for stabilizing an arylcarboxylic acid, which comprises adding a heterocyclic base to the arylcarboxylic acid or a pharmacologically acceptable salt thereof, a stabilizer thereof and an aqueous solution containing a stabilized arylcarboxylic acid. According to the stabilization method of the present invention, arylcarboxylic acid and pharmacologically acceptable salts thereof, particularly pranoprofen, can be stabilized at every temperature range, particularly at lower temperatures, thereby making the production of an aqueous solution to be used as an eye drop, nasal drop, ear drop and the like possible.

4 Claims, No Drawings

METHOD FOR STABILIZING ARYLCARBOXYLIC ACID, STABILIZER THEREOF AND AQUEOUS SOLUTION CONTAINING STABILIZED ARYLCARBOXYLIC ACID

This application is a continuation of Ser. No. 09/885,096 filed June 21, 2001 now abandoned, which is a divisional of Ser. No. 09/017,626 filed Feb. 2, 1998, now issued as U.S. Pat. No. 6,274,592.

TECHNICAL FIELD OF THE INVENTION

The present invention relates to a method for stabilizing arylcarboxylic acid, which is an acidic compound and which has an antiinflammatory activity, or a pharmacologically acceptable salt thereof, a stabilizer thereof and an aqueous solution containing a stabilized arylcarboxylic acid.

BACKGROUND OF THE INVENTION

Arylcarboxylic acid and pharmacologically acceptable salts thereof have been known to be extremely superior antiinflammatory agents. However, said arylcarboxylic acids, particularly pranoprofen, diclofenac and bromfenac, are associated with a problem that they become unstable in an aqueous solution.

Arylcarboxylic acid and pharmacologically acceptable salts thereof have been also known to be stabilized by adding an antioxidant, by adjusting the pH, concentration and ionic strength thereof, by shutting out the light, and the like. These methods, nevertheless, cannot provide sufficient stability at lower temperatures.

Thus, an aqueous solution has not been provided which contains an arylcarboxylic acid or a pharmacologically acceptable salt thereof, particularly pranoprofen, dicrofenac or bromfenac, and which has sufficient stability at lower temperatures.

While WO9632941A1 discloses pranoprofen combined with an organic amine, it does not disclose the heterocyclic base to be used in the present invention.

SUMMARY OF THE INVENTION

It is therefore an object of the present invention to provide a method for stabilizing an arylcarboxylic acid and a pharmacologically acceptable salt thereof.

Another object of the present invention is to provide a stabilizer of an arylcarboxylic acid and a pharmacologically acceptable salt thereof, which contains a heterocyclic base.

Yet another object of the present invention is to provide an aqueous solution containing a solubilized arylcarboxylic acid and a heterocyclic base.

According to the present invention, it has now been found that the addition of a heterocyclic base to an arylcarboxylic acid or a pharmacologically acceptable salt thereof leads to successful stabilization thereof, particularly pranoprofen, at every temperature range, particularly at low temperatures.

Thus, the present invention provides the following.

(1) A method for stabilizing an arylcarboxylic acid or a pharmacologically acceptable salt thereof, which comprises adding a heterocyclic base of the formula (II):

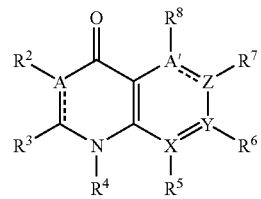

wherein

A and A' are each a carbon atom or a nitrogen atom;

X is a carbon atom or a nitrogen atom;

Y and Z are each a carbon atom or Y and Z may combinedly form CH;

$R^2$, $R^3$, $R^4$, $R^5$, $R^6$, $R^7$ and $R^8$ may be the same or different and each is a hydrogen atom, a halogen, a carboxyl group, an optionally substituted lower alkyl group, an optionally substituted cycloalkyl group, an optionally substituted acyl group, an optionally substituted aryl group or an optionally substituted heterocyclic group, wherein $R^4$ and $R^5$ may form a 4- to 6-membered heterocyclic group with the adjacent nitrogen atom and X, and $R^6$ and $R^7$ may form a 4- to 6-membered heterocyclic group with the adjacent Y and Z, provided that when X is a nitrogen atom, $R^5$ is void; and

is a single bond or a double bond, provided that when A is a carbon atom, Y and Z are each CH and

----- is a double bond, and when A is a nitrogen atom, Y and Z combinedly form CH and

----- is a single bond, to an arylcarboxylic acid of the formula (I):

$$L^1\text{-}R^1 \text{ COOH} \qquad (I)$$

wherein $L^1$ is an optionally substituted heterocyclic group or aryl group having not more than 14 carbon atoms; and $R^1$ is an optionally substituted alkyl group having not more than 4 carbon atoms or a single bond, or a pharmacologically acceptable salt thereof.

(2) The method of (1) above, wherein the heterocyclic base is a purine base of the formula (III):

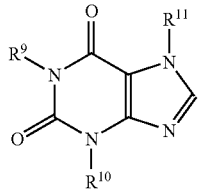

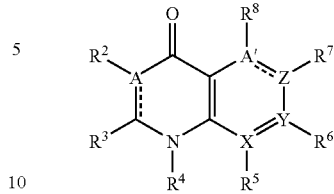

wherein
$R^9$, $R^{10}$ and $R^{11}$ may be the same or different and each is a hydrogen atom or an optionally substituted alkyl group, or a pharmacologically acceptable salt thereof.

(3) The method of (2) above, wherein the purine base is at least one compound selected from the group consisting of caffeine, theobromine and theophylline.

(4) The method of (1) above, wherein the heterocyclic base is a pyridonecarboxylic acid of the formula (IV):

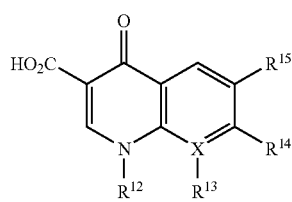

wherein
X is as defined above; and
$R^{12}$, $R^{13}$ $R^{14}$ and $R^{15}$ may be the same or different and each is a hydrogen atom, a halogen, a carboxyl group, an optionally substituted lower alkyl group, an optionally substituted cycloalkyl group, an optionally substituted acyl-group, an optionally substituted aryl group or an optionally substituted heterocyclic group;
wherein $R^{12}$ and $R^{13}$ may form a 4- to 6-membered heterocyclic group with the adjacent nitrogen atom and X, and $R^{14}$ and $R^{15}$ may form a 4- to 6-membered heterocyclic group with the adjacent carbon atom, provided that when X is a nitrogen atom, $R^{13}$ is void, or a pharmacologically acceptable salt thereof.

(5) The method of (4) above, wherein the pyridonecarboxylic acid is at least one compound selected from the group consisting of lomefloxacin, norfloxacin, ofloxacin, enoxacin, ciprofloxacin and tosufloxacin.

(6) The method of (1) above, wherein the arylcarboxylic acid Is at least one compound selected from the group consisting of ibuprofen, diclofenac, 2-naphthoic acid, 2-naphthylacetic acid, 2-naphthoxyacetic acid, bromfenac, pranoprofen, salicylic acid, aspirin, flufenisal, ibufenac, alclofenac, flurbiprofen, ketoprofen, naproxen, mefenamic acid, niflumic acid, metiazinic acid, protizinic acid, clonixin, indomethacin and fenclozic acid.

(7) The method of (1) above, wherein the heterocyclic base is added in a proportion of 0.001-5 parts by weight per 100 parts by weight of the arylcarboxylic acid.

(8) A stabilizer of an arylcarboxylic acid or a pharmacologically acceptable salt thereof, which comprises, as an active ingredient, a heterocyclic base of the formula (II):

wherein
A and A' are each a carbon atom or a nitrogen atom;
X is a carbon atom or a nitrogen atom;
Y and Z are each a carbon atom or Y and Z may combinedly form CH;
$R^2$, $R^3$, $R^4$, $R^5$, $R^6$, $R^7$ and $R^8$ may be the same or different and each is a hydrogen atom, a halogen, a carboxyl group, an optionally substituted lower alkyl group, an optionally substituted cycloalkyl group, an optionally substituted acyl group, an optionally substituted aryl group or an optionally substituted heterocyclic group,
wherein $R^4$ and $R^5$ may form a 4- to 6-membered heterocyclic group with the adjacent nitrogen atom and X, and $R^6$ and $R^7$ may form a 4- to 6-membered heterocyclic group with the adjacent Y and Z,
provided that when X is a nitrogen atom, $R^5$ is void; and

----- is a single bond or a double bond,
provided that when A is a carbon atom, Y and Z are each CH and

----- is a double bond, and when A is a nitrogen atom, Y and Z combinedly form CH and

----- is a single bond.

(9) The stabilizer of (8) above, wherein the heterocyclic base is a purine base of the formula (III):

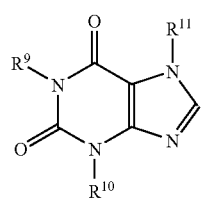

wherein
$R^9$, $R^{10}$ and $R^{11}$ may be the same or different and each is a hydrogen atom or an optionally substituted alkyl group, or a pharmacologically acceptable salt thereof.

(10) The stabilizer of (9) above, wherein the purine base is at least one compound selected from the group consisting of caffeine, theobromine and theophylline.

(11) The stabilizer of (8) above, wherein the heterocyclic base is a pyridonecarboxylic acid of the formula (IV):

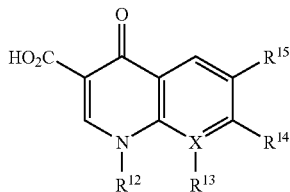

(IV)

wherein
X is as defined above; and
$R^{12}$, $R^{13}$, $R^{14}$ and $R^{15}$ may be the same or different and each is a hydrogen atom, a halogen, a carboxyl group, an optionally substituted lower alkyl group, an optionally substituted cycloalkyl group, an optionally substituted acyl group, an optionally substituted aryl group or an optionally substituted heterocyclic group;
  wherein $R^{12}$ and $R^{13}$ may form a 4- to 6-membered heterocyclic group with the adjacent nitrogen atom and X, and $R^{14}$ and $R^{15}$ may form a 4- to 6-membered heterocyclic group with the adjacent carbon atom, provided that when X is a nitrogen atom, $R^{13}$ is void, or a pharmacologically acceptable salt thereof.

(12) The stabilizer of (11) above, wherein the pyridonecarboxylic acid is at least one compound selected from the group consisting of lomefloxacin, norfloxacin, ofloxacin, enoxacin, ciprofloxacin and tosufloxacin.

(13) The stabilizer of (8) above, wherein the arylcarboxylic acid is at least one compound selected from the group consisting of ibuprofen, diclofenac, 2-naphthoic acid, 2-naphthylacetic acid, 2-naphthoxyacetic acid, bromfenac, pranoprofen, salicylic acid, aspirin, flufenisal, ibufenac, alclofenac, flurbiprofen, ketoprofen, naproxen, mefenamic acid, niflumic acid, metiazinic acid, protizinic acid, clonixin, indomethacin and fenclozic acid.

(14) The stabilizer of (8) above, wherein the heterocyclic base is contained in a proportion of 0.001-5 parts by weight per 100 parts by weight of the arylcarboxylic acid.

(15) An aqueous solution containing an arylcarboxylic acid or a pharmacologically acceptable salt thereof stabilized by the method of (1) above and a heterocyclic base of the formula (II):

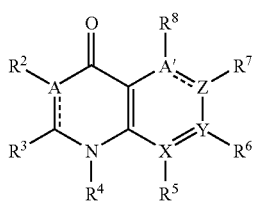

(II)

wherein
A and A' are each a carbon atom or a nitrogen atom;
X is a carbon atom or a nitrogen atom;
Y and Z are each a carbon atom or Y and Z may combinedly form CH;
$R^2$, $R^3$, $R^4$, $R^5$, $R^6$, $R^7$ and $R^8$ may be the same or different and each is a hydrogen atom, a halogen, a carboxyl group, an optionally substituted lower alkyl group, an optionally substituted cycloalkyl group, an optionally substituted acyl group, an optionally substituted aryl group or an optionally substituted-heterocyclic group,
  wherein $R^4$ and $R^5$ may form a 4- to 6-membered heterocyclic group with the adjacent nitrogen atom and X, and $R^6$ and $R^7$ may form a 4- to 6-membered heterocyclic group with the adjacent Y and Z,
  provided that when X is a nitrogen atom, $R^5$ is void; and

----- is a single bond or a double bond,
provided that when A is a carbon atom, Y and Z are each CH and

----- is a double bond, and when A is a nitrogen atom, Y and Z combinedly form CH and

----- is a single bond.

(16) The aqueous solution of (15) above, wherein the heterocyclic base is a purine base of the formula (III):

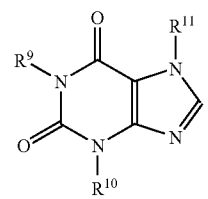

(III)

wherein
$R^9$, $R^{10}$ and $R^{11}$ may be the same or different and each is a hydrogen atom or an optionally substituted alkyl group,
or a pharmacologically acceptable salt thereof.

(17) The aqueous solution of (16) above, wherein the purine base is at least one compound selected from the group consisting of caffeine, theobromine and theophylline.

(18) The aqueous solution of (15) above, wherein the heterocyclic base is a pyridonecarboxylic acid of the formula (IV):

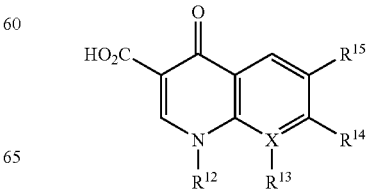

(IV)

wherein

X is as defined above; and $R^{12}$, $R^{13}$, $R^{14}$ and $R^{15}$ may be the same or different and each is a hydrogen atom, a halogen, a carboxyl group, an optionally substituted lower alkyl group, an optionally substituted cycloalkyl group, an optionally substituted acyl group, an optionally substituted aryl group or an optionally substituted heterocyclic group;

wherein $R^{12}$ and $R^{13}$ may form a 4- to 6-membered heterocyclic group with the adjacent nitrogen atom and X, and $R^{14}$ and $R^{15}$ may form a 4- to 6-membered heterocyclic group with the adjacent carbon atom, provided that when X is a nitrogen atom, $R^{13}$ is void, or a pharmacologically acceptable salt thereof.

(19) The aqueous solution of (18) above, wherein the pyridonecarboxylic acid is at least one compound selected from the group consisting of lomefloxacin, norfloxacin, .ofloxacin, enoxacin, ciprofloxacin and tosufloxacin.

(20) The aqueous solution of (15) above, wherein the arylcarboxylic acid is at least one compound selected from the group consisting of ibuprofen, diclofenac, 2-naphthoic acid, 2-naphthylacetic acid, 2-naphthoxyacetic acid, bromfenac, pranoprofen, salicylic acid, aspirin, flufenisal, ibufenac, alclofenac, flurbiprofen, ketoprofen, naproxen, mefenamic acid, niflumic acid, metiazinic acid, protizinic acid, clonixin, indomethacin and fenclozicacid.

(21) The aqueous solution of any one of the above (15) to (20), which is an eye drop.

(22) The aqueous solution of any one of the above (15) to (20), which is a nasal drop.

(23) The aqueous solution of any one of the above (15) to (20), which is an ear drop.

DETAILED DESCRIPTION OF THE INVENTION

The stabilizing method of the present invention comprises the addition of a stabilizer containing a heterocyclic base as an active ingredient to an arylcarboxylic acid, which is an acidic compound and which has an antiinflammatory activity, or a pharmacologically acceptable salt thereof. For example, a heterocyclic base is added to an arylcarboxylic acid or a pharmacologically acceptable salt thereof.

To be specific, an arylcarboxylic acid and a heterocyclic base are dissolved in water and the pH thereof is adjusted with boric acid, acetic acid, phosphoric acid and the like, which is followed by lyophilization where necessary.

While the pH varies depending on the kind of arylcarboxylic acid, it is generally 5-9, preferably about 6-8.

Said heterocyclic base may be any as long as it has the following formula (II):

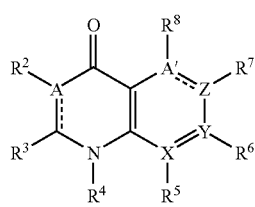

(II)

wherein

A and A' are each a carbon atom or a nitrogen atom;

X is a carbon atom or a nitrogen atom;

Y and Z are each a carbon atom or Y and Z may combinedly form CH;

$R^2$, $R^3$, $R^4$, $R^5$, $R^6$, $R^7$ and $R^8$ may be the same or different and each is a hydrogen atom, a halogen, a carboxyl group, an optionally substituted lower alkyl group, an optionally substituted cycloalkyl group, an optionally substituted acyl group, an optionally substituted aryl group or an optionally substituted heterocyclic group, wherein $R^4$ and $R^5$ may form a 4- to 6-membered heterocyclic group with the adjacent nitrogen atom and X, and $R^6$ and $R^7$ may form a 4- to 6-membered heterocyclic group with the adjacent Y and Z, provided that when X is a nitrogen atom, $R^5$ is void; and

----- is a single bond or a double bond, provided that when A is a carbon atom, Y and Z are each CH and

----- is a double bond, and when A is a nitrogen atom, Y and Z combinedly form CH and

----- is a single bond.

The alkyl of the "optionally substituted lower alkyl group" has 1 to 6 carbon atoms, and may be a linear or branched one, such as methyl, ethyl, propyl, isopropyl, butyl, isobutyl, tert-butyl, pentyl, isopentyl, neopentyl, tert-pentyl, hexyl, isohexyl, neohexyl and the like.

The cycloalkyl of the "optionally substituted cycloalkyl group" has 3 to 9 carbon atoms, and is exemplified by cyclopropyl, cyclobutyl, cyclopentyl, cyclohexyl, cycloheptyl and the like.

The substituents of the above-mentioned lower alkyl group and cycloalkyl group include lower alkyl group, halogen and the like.

The lower acyl of the "optionally substituted lower acyl group" may be, for example, formyl group, acetyl group, propionyl group, butyryl group, isobutyryl group, valeryl group, benzoyl group, naphthoyl group, toluoyl group, salicyloyl group and the like.

The above-mentioned acyl may be substituted by suitable substituents which may be the same or different, such as lower alkyl (e.g., methyl, ethyl, propyl, etc.);

lower alkoxy (e.g., methoxy, ethoxy, propoxy, etc.);

lower alkylthio (e.g., methylthio, ethylthio, etc.);

lower alkylamino (e.g., methylamino, ethylamino, propylamino and the like);

cyclo(lower)alkyl such as cyclo($C_3$-$C_6$)alkyl (e.g., cyclopentyl, cyclohexyl and the like);

cyclo(lower)alkenyl such as cyclo($C_3$-$C_6$)alkenyl (e.g., cycloxenyl, cyclohexadienyl and the like);

halogen (e.g., fluorine, chlorine, bromine and iodine);

amino; amino protecting group; hydroxy; protected hydroxy; cyano; nitro; carboxy; protected carboxy; sulfo; sulfamoyl; imino; oxo;

amino(lower)alkyl (e.g., aminomethyl, aminoethyl and the like), carbamoyloxy, hydroxy(lower)alkyl (e.g., hydroxymethyl, 1- or 2-hydroxyethyl, 1- or 2- or 3-hydroxypropyl and the like); and the like.

The aryl of the "optionally substituted aryl group" is exemplified by phenyl, naphthyl and the like, with preference given to naphthyl.

The heterocyclic group of the optionally substituted heterocyclic group may contain, besides the carbon atom, at least one hetero atom selected from the group consisting of a nitrogen atom, sulfur atom and oxygen atom, as the atom constituting the ring, and may be a saturated or unsaturated, heteromonocyclic or heteropolycyclic group.

The preferable heterocyclic groups are the following:

3- to 6-membered unsaturated heteromonocyclic group having 1 to 4 nitrogen atoms, such as pyrrolyl, pyrrolinyl, imidazolyl, pyrazolyl, pyridyl, pyrimidinyl, pyrazinyl, pyridazinyl, triazolyl (e.g., 4H-1,2,4-triazolyl, 1H-1,2,3-triazolyl, 2H-1,2,3-triazolyl and the like), tetrazolyl (e.g., 1H-tetrazolyl, 2H-tetrazolyl and the like), triazinyl (e.g., 1,2,4-triazinyl and the like), and the like;

3- to 7-membered saturated heteromonocyclic group having 1 to 4 nitrogen atoms, such as pyrrolidinyl, imidazolidinyl, piperidinyl, piperazinyl, homopiperazinyl, and the like;

saturated heteropolycyclic group having 1 to 4 nitrogen atoms, such as quinuclidinyl and the like;

unsaturated heteropolycyclic group having 1 to 5 nitrogen atoms, such as indolyl, isoindolyl, 3H-indolyl, indolizinyl, benzoimidazolyl, quinolyl, isoquinolyl, indazolyl, phthalazinyl, naphthyridinyl, quinoxalinyl, quinazolinyl, cinnolinyl, benzotriazolyl, tetrazolo-pyridazinyl (e.g., tetrazolo[1,5-b]pyridazinyl and the like), pteridinyl, carbazolyl, phenanthrinidyl, acridinyl, perimidyl, and the like;

3- to 6-membered unsaturated heteromonocyclic group having 1 to 3 nitrogen atoms and 1 or 2 oxygen atoms, such as oxazolyl, isooxazolyl, oxadiazolyl (e.g., 1,2,4-oxadiazolyl, 1,3,4-oxadiazolyl, 1,2,5-oxadiazolyl and the like), and the like;

3- to 6-membered saturated heteromonocyclic group having 1 to 3 nitrogen atoms and 1 or 2 oxygen atoms, such as morpholinyl, sydnolyl, and the like;

unsaturated condensed heterocyclic group having 1 to 3 nitrogen atoms and 1 or 2 oxygen atoms, such as benzofurazanyl, benzoxazolyl, benzoxazinyl, benzoxadiazolyl, and the like;

3- to 6-membered unsaturated condensed heterocyclic group having 1 to 3 nitrogen atoms and 1 or 2 sulfur atoms, such as thiazolyl, isothiazolyl, thiadiazolyl (e.g., 1,2,4-thiadiazolyl, 1,3,4-thiadiazolyl, 1,2,5-thiadiazolyl and the like), and the like;

3- to 6-membered saturated heteromonocyclic group having 1 to 3 nitrogen atoms and 1 or 2 sulfur atoms, such as thiazolidinyl and the like;

unsaturated condensed heterocyclic group having 1 to 3 nitrogen atoms and 1 or 2 sulfur atoms, such as benzothiazolyl, benzothiadiazolyl, and the like;

3- to 6-membered unsaturated heteromonocyclic group having 1 oxygen atom, such as furyl, pyranyl and the like;

3- to 6-membered unsaturated heteromonocyclic group having 1 or 2 sulfur atoms, such as thienyl, dihydrothienyl, and the like;

unsaturated condensed heterocyclic group having 1 or 2 sulfur atoms, such as benzothienyl and the like; and the like.

The aryl group and heterocyclic group are optionally substituted by one or more substituents selected from the group consisting of hydroxyl group, halogen atom, aliphatic alkyl group, aromatic alkyl group, aliphatic carboxylic acid group, aromatic carboxylic acid group, aliphatic carboxylate group, aromatic carboxylate group, aliphatic ether group, aromatic ether group, aliphatic alcohol group, aromatic alcohol group, aliphatic aldehyde group, aromatic aldehyde group, aliphatic amino group, aromatic amino group and the like, which are optionally substituted by halogen atom.

The 4- to 6-membered ring formed by $R^4$ and $R^5$ with the adjacent nitrogen atom and X, and the 4- to 6-membered heterocyclic ring formed by $R^6$ and $R^7$ with the adjacent Y and Z may be, for example, thienyl group, furyl group, pyrrolyl group, imidazolyl group, pyrazolyl group, thiazolyl group, isothiazolyl group, oxazolyl group, isooxazolyl group, oxadiazolyl group, thiadiazolyl group, triazolyl group, pyridyl group, pyrazinyl group, pyrimidinyl group, pyridazinyl group, triazinyl group, dithiazolyl group, dioxolanyl group (e.g., 1,3-dioxolanyl group), dithiolyl group, pyrrolidinyl group, thiaziadinyl group, dithiaziadinyl group, morpholinyl group, oxazinyl group, thiazinyl group, piperazinyl group, piperidinyl group, pyranyl group, thiopyranyl group and the like.

The above-mentioned heterocyclic base is specifically exemplified by a purine base having a purine skeleton and a pyridonecarboxylic acid having a pyridine skeleton or pyridazine skeleton.

The purine base is a compound of the formula (II) wherein A is a nitrogen atom, Y and Z may combinedly form CH and

----- is a single bond. It is represented by the formula (III):

(III)

wherein $R^9$, $R^{10}$ and $R^{11}$ may be the same or different and each is a hydrogen atom or an optionally substituted alkyl group, and exemplified by caffeine, theobromine, theophylline and salts thereof.

The pyridonecarboxylic acid is a compound of the formula (II) wherein A is a carbon atom, Y and Z are each CH and

----- is a double bond. It is represented by the formula (IV):

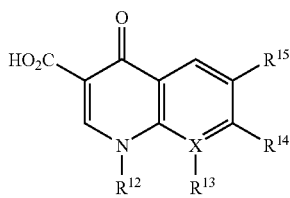

(IV)

wherein
X is as defined above; and
$R^{12}$, $R^{13}$, $R^{14}$ and $R^{15}$ may be the same or different and each is a hydrogen atom, a halogen, a carboxyl group, an optionally substituted lower alkyl group, an optionally substituted cycloalkyl group, an optionally substituted acyl group, an optionally substituted aryl group or an optionally substituted heterocyclic group;
wherein $R^{12}$ and $R^{13}$ may form a 4- to 6-membered heterocyclic group with the adjacent nitrogen atom and X, and $R^{14}$ and $R^{15}$ may form a 4- to 6-membered heterocyclic group with the adjacent carbon atom, provided that when X is a nitrogen atom, $R^{13}$ is void.

Examples of the pyridonecarboxylic acid include norfloxacin: [1-ethyl-6-fluoro-1,4-dihydro-4-oxo-7-(1-piperazinyl)-3-quinolinecarboxylic acid], of loxacin: [(±)-9-fluoro-2,3-dihydro-3-methyl-10-(4-methyl-1-piperazinyl)-7-oxo-7H-[1,2,3-de]-1,4-benzoxazine-6-carboxylic acid], enoxacin: [1-ethyl-6-fluoro-1,4-dihydro-4-oxo-7-(1-piperazinyl)-1,8-naphthyridine-3-carboxylic acid], cinoxacin: [1-ethyl-1,4-dihydro-4-oxo-[1,3]-dioxolo[4,5-g]cinnoline-3-carboxylic acid], ciprofloxacin: [1-cyclopropyl-6-fluoro-1,4-dihydro-4-oxo-7-(1-piperazinyl)-3-quinoline-carboxylic acid], sparfloxacin: [5-amino-1-cyclopropyl-7-(cis-3,5-dimethyl-1-piperazinyl)-6,8-difluoro-1,4-dihydro-4-oxoquinoline-3-carboxylic acid], tosufloxacin: [(±)-7-(3-amino-1-pyrrolidinyl)-1-(2,4-difluorophenyl)-6-fluoro-1,4-dihydro-4-oxo-1-naphthyridine-3-carboxylic acid], fleroxacin: [6,8-difluoro-1-(2-fluoroethyl)-1,4-dihydro-7-(4-methyl-1-piperazinyl)-4-oxo-3-quinolinecarboxylic acid], levofloxacin: [(−)-(S)-9-fluoro-2,3-dihydro-3-methyl-10-(4-methyl-1-piperazinyl)-7-oxo-7H-pyrido[1,2,3-de][1,4]benzoxazine-6-carboxylic acid], lomeflo-xacin: [1-ethyl-6,8-difluoro-1,4-dihydro-7-(3-methyl-1-piperazinyl)-4-oxo-3-quinolinecarboxylic acid], 5,8-dihydro-8-ethyl-2-(1-piperazinyl)-5-oxopyrido[2,3-d]pyrimidinecarboxylic acid, 7-(3-amino-1-pyrrolidinyl)-1-ethyl-6-fluoro-1,4-dihydro-4-oxo-1,8-naphthyridine-3-carboxylic acid, 7-(3-amino-1-pyrrolidinyl)-1-cyclopropyl-6-fluoro-1,4-dihydro-4-oxo-1,8-naphthyridine-3-carboxylic acid, 1-cyclopropyl-6-fluoro-7-(3-methyl-amino-1-pyrrolidinyl)-1,4-dihydro-4-oxo-1,8-naphthyridine-3-carboxylic acid, 7-(3-amino-3-methyl-1-pyrrolidinyl)-1-cyclopropyl-6-fluoro-1,4-dihydro-4-oxo-1,8-naphthyridine-3-carboxylic acid and the like, and salts thereof and the like.

The pharmacologically acceptable salts of purine base and pyridonecarboxylic acid include, for example, acid addition salts with inorganic acid such as hydrochloric acid, sulfuric acid, phosphoric acid and the like, organic acid such as acetic acid, lactic acid, succinic acid, methanesulfonic acid, maleic acid, malonic acid, gluconic acid and the like, or amino acid such as aspartic acid, glutamic acid and the like; metal salts such as sodium salt, potassium salt and the like; and the like.

The arylcarboxylic acid to be used for the stabilization of the present invention may be any compound as long as it has the following formula (I):

$$L^1-R^1COOH \qquad (I)$$

wherein
$L^1$ is an optionally substituted heterocyclic group or aryl group having not more than 14 carbon atoms; and
$R^1$ is an optionally substituted alkyl group having not more than 4 carbon atoms or a single bond.

The heterocyclic group in the optionally substituted heterocyclic group having not more than 14 carbon atoms may be exemplified by those mentioned above, and the substituents of said heterocyclic group are also exemplified by those mentioned above.

The aryl of the "optionally substituted aryl group having not more than 14 carbon atoms" may be exemplified by those mentioned above, and the substituents of said aryl group are also exemplified by those mentioned above.

The alkyl of the "optionally substituted alkyl group having not more than 4 carbon atoms" may be, for example, a linear or branched one such as methyl, ethyl, propyl, isopropyl, butyl, isobutyl, tert-butyl and the like.

Examples of the arylcarboxylic acid include naphthoic acid-related compounds, salicylic acid-related compounds, phenylacetic acid-related compounds, pyrazolone-related compounds, anthranilic acid-related compounds, indoleacetic acid-related compounds, fenclozic acid-related compounds and salts thereof and the like.

Examples of the naphthoic acid-related compounds include 2-naphthoic acid, 2-naphthylacetic acid, 2-naphthoxyacetic acid and the like.

Examples of the salicylic acid-related compounds include salicylic acid, aspirin, flufenisal, ethenzamide, benorylate and the like.

Examples of the phenylacetic acid-related compounds include ibufenac, alclofenac, flurbiprofen, ketoprofen, naproxen, ibuprofen, bromfenac, pranoprofen, namoxylate, fenoprofen and the like.

Examples of the pyrazolone-related compounds include aminopyrine, phenylbutazone, azapropazone, cinopentazone and the like.

Examples of the anthranilic acid-related compounds include mefenamic acid, niflumic acid, diclofenac, metiazinic acid, protizinic acid, clonixin, flufenamic acid, ketoprofen and the like.

Examples of the indoleacetic acid-related compounds include indomethacin, intrazole and the like.

The amount of the heterocyclic base to be added to the arylcarboxylic acid or a pharmacologically acceptable salt thereof is preferably about 0.001-5 parts by weight per 100 parts by weight of the arylcarboxylic acid or pharmacologically acceptable salt thereof.

The stabilizer of the arylcarboxylic acid and a pharmacologically acceptable salt thereof contains a heterocyclic base as an active ingredient, and the amount thereof is about the same as the amount mentioned above.

The solvent to be used for the aqueous solution of the present invention may be, for example, purified water, particularly distilled water for injection. The concentration of the active ingredient of the aqueous solution, i.e. arylcarboxylic acid, can be markedly increased by a heterocyclic base, preferably to 0.1-10 (w/v) %.

The heterocyclic base to be used for the aqueous solution of the present invention may be those mentioned above.

Said aqueous solution may contain various additives as appropriate, such as buffer, isotonizing agent, solubilizer, antiseptic, thickener, chelating agent, aromatic and the like.

Examples of the buffer include phosphate buffer, borate buffer, citrate buffer, tartrate buffer, acetate buffer, amino acid and the like.

Examples of the isotonizing agent include sugars such as sorbitol, glucose, mannitol and the like, polyhydric alcohols such as glycerol, propylene glycol and the like, salts such as sodium chloride and the like, and the like.

Examples of the solubilizer include non-ionic surfactants such as polyoxyethylenesorbitan monooleate, polyoxyethyleneoxystearic acid triglyceride, polyethylene glycol, polyoxyethylene hydrogenated castor oil and the like, and the like.

Examples of the antiseptic include quaternary ammonium salts such as benzalkonium chloride, benzethonium chloride, cetylpyridinium chloride and the like, p-hydroxybenzoates such as methyl p-hydroxybenzoate, ethyl p-hydroxybenzoate, propyl p-hydroxybenzoate, butyl p-hydroxybenzoate and the like, benzyl alcohol, phenethyl alcohol, sorbic acid, salts thereof, thimerosal, chlorobutanol, sodium dehydroacetate and the like.

Examples of the thickener include polyvinylpyrrolidone, hydroxyethylcellulose, hydroxypropylcellulose, methylcellulose, hydroxypropylmethylcellulose, carboxymethylcellulose, salts thereof and the like.

Examples of the chelating agent include sodium edetate, citric acid and the like.

Examples of the aromatic include 1-menthol, borneol, camphor, eucalyptus oil and the like.

The aqueous solution of the present invention is used as an eye drop, nasal drop or ear drop. When it is used as an eye drop, its pH is generally adjusted to about 3.5-8.5, preferably about 6-7, when it is used as a nasal drop, its pH is generally adjusted to about 3.5-8.5, preferably about 6-7, and when it is used as an ear drop, its pH is generally adjusted to about 3.5-8.5, preferably about 6-7.

While the method for producing the aqueous solution of the present invention varies depending on the kind of a desired solution, a known method can be used to produce such aqueous solution.

When the aqueous solution of the present invention is used as an eye drop, for example, the dose thereof need only be sufficient to effectively suppress an inflammation in the eye, and may vary according to symptoms, the kind of inflammation, the patients (human or animal) in need of said solution and the like. A typical dose is 20-200 μL, preferably 50-100 μL, which may be administered 1 to 12 times a day.

The present invention is described in more detail by way of Examples and Experimental Examples, which should not be construed as limiting the invention.

EXPERIMENTAL EXAMPLE 1

Stabilization of Pranoprofen-1

Solutions (Examples 1-3 below) of 0.5 w/v % pranoprofen were respectively charged in 5 ml colorless glass ampoules, and allowed to stand at 80° C. for 1 week and 2 weeks, at 60° C. for 1 week and 2 weeks, and at 4° C. for 1 week. The percentage of residual pranoprofen in the ampoules after standing was determined by high performance liquid chromatography. The results are shown in Table 1. The values in the Table are relative to the amount of pranoprofen when it was prepared, which was taken as 100.

TABLE 1

| temperature-period | residual pranoprofen (%) | | | |
|---|---|---|---|---|
| | w/o addition | norfloxacin | ofloxacin | enoxacin |
| 80° C.-1 W | 95.4 | 91.0 | 99.5 | 96.7 |
| 80° C.-2 W | 93.0 | 85.0 | 100.4 | 95.9 |
| 60° C.-1 W | 98.7 | 98.0 | 99.8 | 99.2 |
| 60° C.-2 W | 98.5 | 93.8 | 98.8 | 98.4 |
| 4° C.-1 W | 87.5 | 99.8 | 99.9 | 99.2 |

EXPERIMENTAL EXAMPLE 2

Stabilization of Pranoprofen-2

Solutions (Example 4) of 0.5 w/v % pranoprofen, containing boric acid (1.6 w/v %), caffeine (0.3 w/v %) and sterile purified water (appropriate amount) were respectively charged in 5 ml colorless glass ampoules, and allowed to stand at 80° C. for 2 weeks, at 60° C. for 1 week, 2 weeks and 4 weeks, and at 4° C. for 1 week and 1 month. The percentage of residual pranoprofen in the ampoules after standing was determined by high performance liquid chromatography. The results are shown in Table 2. The values in the Table are relative to the amount of pranoprofen when it was prepared, which was taken as 100.

TABLE 2

| temperature-period | residual pranoprofen (%) | |
|---|---|---|
| | w/o addition | caffeine |
| 80° C.-2 W | 91.9 | 94.2 |
| 60° C.-1 W | 100.1 | 101.3 |
| 60° C.-2 W | 99.2 | 100.9 |
| 60° C.-4 W | 96.7 | 99.5 |
| 4° C.-1 W | 95.0 | 100.8 |
| 4° C.-1 M | 93.5 | 97.8 |

As is evident from the results shown in Table 1 and Table 2, pranoprofen was markedly stabilized against heat by the addition of ofloxacin, enoxacin and caffeine. The decomposition of pranoprofen which occurs at low temperatures was significantly suppressed by norfloxacin, ofloxacin, enoxacin and caffeine.

EXAMPLE 1

An eye drop having the following formulation was prepared.

| pranoprofen | 1.0 g |
|---|---|
| norfloxacin | 0.6 g |
| boric acid | 3.2 g |
| sodium hydroxide | appropriate amount |
| sterile purified water | appropriate amount |
| total amount | 200 ml (pH 7) |

EXAMPLE 2

An ear drop having the following formulation was prepared.

| | |
|---|---|
| pranoprofen | 1.0 g |
| ofloxacin | 0.6 g |
| boric acid | 3.2 g |
| sodium hydroxide | appropriate amount |
| sterile purified water | appropriate amount |
| total amount | 200 ml (pH 7) |

EXAMPLE 3

A nasal drop having the following formulation was prepared.

| | |
|---|---|
| pranoprofen | 1.0 g |
| enoxacin | 0.6 g |
| phosphoric acid | 0.1 g |
| sodium hydroxide | appropriate amount |
| sterile purified water | appropriate amount |
| total amount | 200 ml (pH 7) |

EXAMPLE 4

An eye drop having the following formulation was prepared.

| | |
|---|---|
| pranoprofen | 0.5 g |
| caffeine | 0.3 g |
| boric acid | 1.6 g |
| sterile purified water | appropriate amount |
| total amount | 100 ml (pH 7) |

EXAMPLE 5

An eye drop having the following formulation was prepared.

| | |
|---|---|
| pranoprofen | 0.1 g |
| ofloxacin | 0.3 g |
| boric acid | 1.8 g |
| sorbic acid | 0.1 g |
| sterile purified water | appropriate amount |
| total amount | 100 ml (pH 7) |

EXAMPLE 6

An eye drop having the following formulation was prepared.

| | |
|---|---|
| pranoprofen | 0.1 g |
| enoxacin | 0.3 g |
| boric acid | 1.8 g |
| benzalkonium chloride | 0.002 g |
| sodium citrate | 0.1 g |
| sterile purified water | appropriate amount |
| total amount | 100 ml (pH 7) |

EXAMPLE 7

An eye drop having the following formulation was prepared.

| | |
|---|---|
| pranoprofen | 0.1 g |
| caffeine | 0.3 g |
| boric acid | 1.8 g |
| benzalkonium chloride | 0.002 g |
| sterile purified water | appropriate amount |
| total amount | 100 ml (pH 7) |

EXAMPLE 8

An ear drop having the following formulation was prepared.

| | |
|---|---|
| pranoprofen | 1.0 g |
| ofloxacin | 0.6 g |
| phosphoric acid | 0.1 g |
| sodium hydroxide | appropriate amount |
| sterile purified water | appropriate amount |
| total amount | 200 ml (pH 7) |

According to the stabilization method of the present invention, arylcarboxylic acid and pharmacologically acceptable salts thereof, particularly pranoprofen, can be stabilized at every temperature range, particularly at lower temperatures, thereby making the production of an aqueous solution to be used as an eye drop, nasal drop, ear drop and the like possible.

This application is based on application No. 21805/1997 filed in Japan, the content of which is incorporated hereinto by reference.

What is claimed is:

1. A method for stabilizing an arylcarboxylic acid or a pharmacologically acceptable salt thereof in an aqueous solution, which comprises adding a pyridonecarboxylic acid selected from (a) a pyridonecarboxylic acid of the formula (IV):

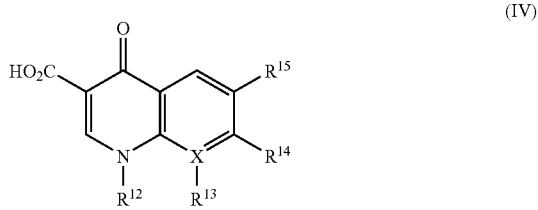

wherein

X is a carbon atom; and $R^{12}$, $R^{13}$, $R^{14}$ and $R^{15}$ are the same or different and each is a hydrogen atom, a halogen, a carboxyl group, an optionally substituted lower alkyl group, an optionally substituted cycloalkyl group, an optionally substituted acyl group, an optionally substituted aryl group or an optionally substituted heterocyclic group;

wherein $R^{12}$ and $R^{13}$ optionally form a 4- to 6-membered heterocyclic group with the adjacent nitrogen atom and X, and $R^{14}$ and $R^{15}$ optionally form a 4- to 6-membered heterocyclic group with the adjacent carbon atom, (b) cinoxacin or (c) sparfloxacin, or a pharmacologically acceptable salt thereof, to an arylcarboxylic acid of the formula (I):

$$L^1\text{-}R^1COOH \qquad (I)$$

wherein $L^1$ is an optionally substituted aryl group having not more than 14 carbon atoms; and $R^1$ is an optionally substituted alkyl group having not more than 4 carbon atoms or a single bond, or a pharmacologically acceptable salt thereof.

2. The method of claim 1, wherein the pyridonecarboxylic acid is at least one compound selected from the group consisting of lomefloxacin, norfloxacin, ofloxacin, ciprofloxacin, fleroxacin and levofloxacin.

3. The method of claim 1, wherein the arylcarboxylic acid is at least one compound selected from the group consisting of ibuprofen, diclofenac, 2-naphthoic acid, 2-naphthylacetic acid, bromfenac, salicylic acid, aspirin, flufenisal, ibufenac, alclofenac, flurbiprofen, ketoprofen, naproxen and mefenamic acid.

4. The method of claim 1, wherein the pyridonecarboxylic acid is added in a proportion of 0.001-5 parts by weight per 100 parts by weight of the arylcarboxylic acid.

* * * * *